US011730707B2

(12) United States Patent
Botella Cubells et al.

(10) Patent No.: US 11,730,707 B2
(45) Date of Patent: Aug. 22, 2023

(54) COMPOUNDS FOR TREATING VON HIPPEL-LINDAU DISEASE

(71) Applicants: CONSEJO SUPERIOR DE INVESTIGACIONES CIENTÍFICAS, Madrid (ES); ALIANZA ESPAÑOLA DE FAMILIAS DE VON HIPPEL-LINDAU-VHL, Olías del Rey (ES)

(72) Inventors: Luisa María Botella Cubells, Madrid (ES); Virginia Albiñana Díaz, Madrid (ES); Karina Villar Gomez-De Las Heras, Olías del Rey (ES)

(73) Assignees: ALIANZA ESPAÑOLA DE FAMILIAS DE VON HIPPEL-LINDAU-VHL, Olías del Rey (ES); CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 471 days.

(21) Appl. No.: 16/636,959

(22) PCT Filed: Aug. 6, 2018

(86) PCT No.: PCT/EP2018/071220
§ 371 (c)(1),
(2) Date: Feb. 6, 2020

(87) PCT Pub. No.: WO2019/030151
PCT Pub. Date: Feb. 14, 2019

(65) Prior Publication Data
US 2020/0323798 A1 Oct. 15, 2020

(30) Foreign Application Priority Data
Aug. 7, 2017 (ES) .............................. ESP201731019

(51) Int. Cl.
*A61K 31/138* (2006.01)
*A61P 35/04* (2006.01)

(52) U.S. Cl.
CPC ............ *A61K 31/138* (2013.01); *A61P 35/04* (2018.01)

(58) Field of Classification Search
CPC ......... A61K 31/138; A61P 35/00; A61P 35/04
See application file for complete search history.

(56) References Cited

FOREIGN PATENT DOCUMENTS

| WO | 2009050567 A2 | 4/2009 |
| WO | 2010117423 A2 | 10/2010 |
| WO | 2011133142 A1 | 10/2011 |

OTHER PUBLICATIONS

Wolter et al., Oncotarget 2014, 161-172.*
D. Cotton et al., "Novel adrenergic receptor inhibitors and their inhibition of stress-induced metastasis of breast cancer," European Journal of Cancer, Nov. 2016, s82-s83, vol. 69.
Office action for corresponding Eurasian patent application 202090452, dated Mar. 28, 2022.
Stella R. O'Donnell et al., "The importance of choice of agonist in studies designed to predict beta 2 : beta 1 adrenoceptor selectivity of antagonists from pA2 values on guinea-pig trachea and atria," Naunyn Schmiedebergs Arch Pharmacol., Sep. 1979, pp. 183-190, vol. 308.
James A. Nathanson, "Beta-adrenergic-sensitive adenylate cyclase in secretory cells of choroid plexus," Science, May 25, 1979, pp. 843-844, vol. 204.
James A. Nathanson, "Cerebral microvessels contain a beta 2-adrenergic receptor," Life Sciences, May 1980, pp. 1793-1799, vol. 26, No. 21.
Kenneth P. Minneman et al., "The pharmacological specificity of beta-1 and beta-2 adrenergic receptors in rat heart and lung in vitro," Mol Pharmacol., Jul. 1979, pp. 21-33, vol. 16.
Kenneth P. Minneman et al., Comparison of beta adrenergic receptor subtypes in mammalian tissues, Journal of Pharmacology and Experimental Therapeutics, Dec. 1979, pp. 502-508, vol. 211, No. 3.
Stella R. O'Donnell et al., "Evidence that ICI 118, 551 is a potent, highly Beta 2-selective adrenoceptor antagonist and can be used to characterize Beta-adrenoceptor populations in tissues," Life Sciences, Aug. 1980, pp. 371-677, vol. 27, No. 8.
Andrew J. Bilski et al., "The Pharmacology of a β2-Selective Adrenoceptor Antagonist (ICI 118,551)," J Cardiovasc Pharmacol., May 1983, pp. 430-437, vol. 5, No. 3.
U. Johansson et al., "On the stereospecificity of the beta2-adrenoceptor blocking properties of prenalterol," J Pharm Pharmacol., Sep. 1980, pp. 659-660, vol. 32, No. 9.
C. Richard Crooks et al., "Synthesis and preliminary biological studies of 4- and 5-[2-hydroxy-3-(isopropylamino)propoxy]benzimidazoles: selective β2 adrenergic blocking agents," J. Med. Chem., Feb. 1979, pp. 210-214, vol. 22, No. 2.
J.L. Imbs et al., "A potent new β2-adrenoceptor blocking agent," Br J. Pharmacol., Jul. 1977, pp. 357-362, vol. 60.
Padam C. Jain et al., "Adrenoceptor blocking agents. 2. 2-(.alpha.-Hydroxyarylmethyl)-3,3-dimethylaziridines, a new class of selective .beta.2-adrenoceptor antagonists," Journal of Medicinal Chemistry, Jan. 1978, vol. 21, No. 1.
Rachels Van Leeuwaarde et al., "Von Hippel-Lindau Syndrome," GeneReviews®, Initial Posting: May 17, 2000, Last Update: Sep. 6, 2018.
Shannon Reagan-Shaw et al., "Dose translation from animal to human studies revisited," The FASEB Journal, Mar. 2007, pp. 659-661, vol. 22.

(Continued)

*Primary Examiner* — Shobha Kantamneni
(74) *Attorney, Agent, or Firm* — Pilloff Passino & Cosenza LLP; Sean A. Passino; Rachel K. Pilloff

(57) ABSTRACT

The invention relates to the use of a selective β2 adrenergic receptor antagonist for treating and preventing a tumor in a patient with von Hippel-Lindau syndrome. In particular, the invention relates to the use of an alkanolamine derivative or a pharmaceutically acceptable acid-addition salt thereof for treating and preventing a hemangioblastoma in VHL syndrome patients.

Figure 1:
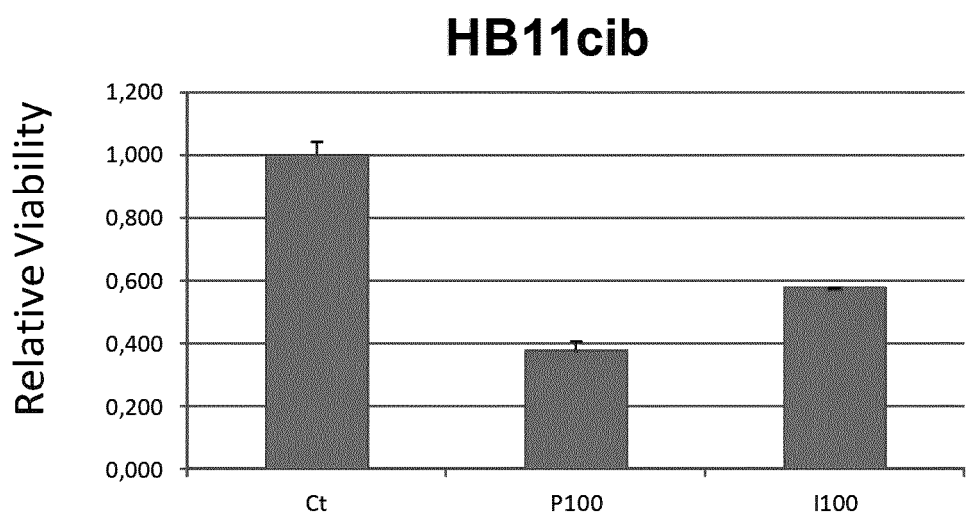

12 Claims, 14 Drawing Sheets
Specification includes a Sequence Listing.

(56) References Cited

OTHER PUBLICATIONS

Pan Pantziarka et al., "Repurposing Drugs in Oncology (ReDO)-Propranolol as an anti-cancer agent," eCancerMedicalscience, Oct. 12, 2016, p. 680, vol. 10.

Virginia Albiñana et al., "Repurposing propranolol as a drug for the treatment of retinal haemangioblastomas in von Hippel-Lindau disease," Orphanet Journal of Rare Diseases, Jun. 29, 2017, vol. 12, No. 1.

Virginia Albiñana et al., "Propranolol reduces viability and induces apoptosis in hemangioblastoma cells from von Hippel-Lindau patients," Orphanet Journal of Rare Diseases, Sep. 22, 2015, vol. 10, No. 1.

International Search Report and Written Opinion for PCT/EP2018/071220, dated Oct. 4, 2018.

* cited by examiner

COMPOUNDS FOR TREATING VON HIPPEL-LINDAU DISEASE

FIELD OF THE INVENTION

The invention relates to the field of therapeutics and prevention, more specifically to the treatment and prevention of von Hippel-Lindau disease.

BACKGROUND OF THE INVENTION

Von Hippel-Lindau (VHL) disease is a rare type of cancer with an incidence of 1 per 36,000 individuals in the general population. VHL is an autosomal dominantly inherited genetic disorder. The disease was first described separately by von Hippel in 1911 and by Lindau in 1926.

The clinical manifestations include multiple benign and malignant tumors that appear throughout the lifespan of the patient: retinal hemangioblastoma, CNS hemangioblastoma, clear cell renal cell carcinoma (CCRCC), pheochromocytoma, pancreatic islet tumor, endolymphatic sac tumors and cysts in testes and broad ligament.

Tumor cells from VHL have lost the von Hippel-Lindau protein function, which leads to a constitutive expression of hypoxia inducible factor (HIF), even in normoxic conditions.

HIF is responsible for activation of genes involved in angiogenesis, metabolism and apoptosis that promote adaptation and survival under low $O_2$ conditions (hypoxia), such as might be found in ischemic tissues and in most solid tumors.

In normoxia, the rapid degradation of HIF is controlled by pVHL binding to hydroxylated residues of HIF-α. Under hypoxic conditions, PHD cannot hydroxylate HIFα subunits that then escape ubiquitin mediated proteolysis, allowing HIFα to accumulate, translocate to the nucleus, and bind to HIFβ. This heterodimer is able to bind specific DNA sequences ("hypoxia responsive elements" or HRE) to activate transcription of more than 200 target genes. Main genes regulated by pVHL are involved in tumor development, angiogenesis (vascular endothelial growth factor [VEGF] and platelet derivative growth factor [PDGF]), cell proliferation or survival (transforming growth factor [TGFα]), regulation of glucose uptake and metabolism (glucose transporter Glut-1) and erythropoiesis (EPO). Other target genes relevant to tumor biology are involved in extracellular matrix formation (matrix metalloproteinase 1 [MMP1]), chemotaxis (stromal cell derived factor 1 [SDF1] and its receptor CXC chemokine receptor 4 [CXCR4], epidermal growth factor receptor [EGFR], Hepatocyte growth factor receptor [HGFR encoded by MET]), pH regulation (carbonic anhydrases IX and XII [CA9 and CA12]), and cell cycle (cyclin D1 [CCND1]).

Thus far, therapeutic options for VHL patients are derived from surgery. The systemic therapy used for metastatic cancers has shown limited response in VHL pancreatic and renal tumors, while CNS tumors do not respond at all.

VHL Spanish Alliance conducted a clinical trial with 7 VHL patients for 12 months, from December 2014 to April 2016. Patients were treated for retina hemangioblastomas with 120 mg of propranolol a day (a suboptimal dose, for many patients under 2 mg/Kg body weight/day). As a result, tumors did not grow in any case during the clinical trial and in some cases visual acuity increased. More interestingly, in 2 cases with exudates from the hemangioblastomas, these disappeared completely between 3 and 6 months of treatment. Low blood pressure was recorded as a side effect (Albiñana et al., 2017) Therefore, the lack of therapies for recurrent disease means there is an urgent requirement for effective drugs with reduced side effects for VHL patients, especially those that halt the progression of tumors and delay surgical treatment.

BRIEF DESCRIPTION OF THE INVENTION

Figure 2:
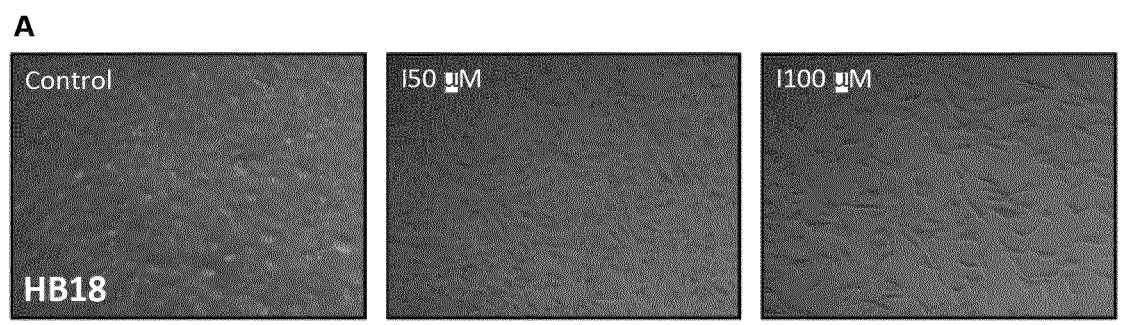
Figure 2:
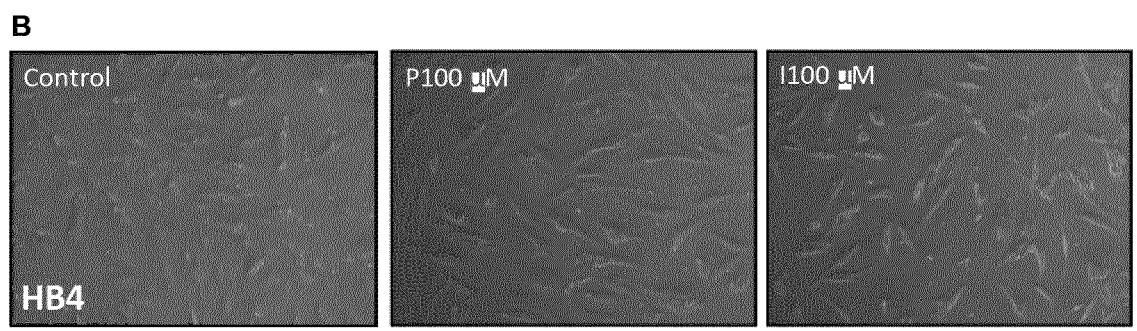
Figure 3:
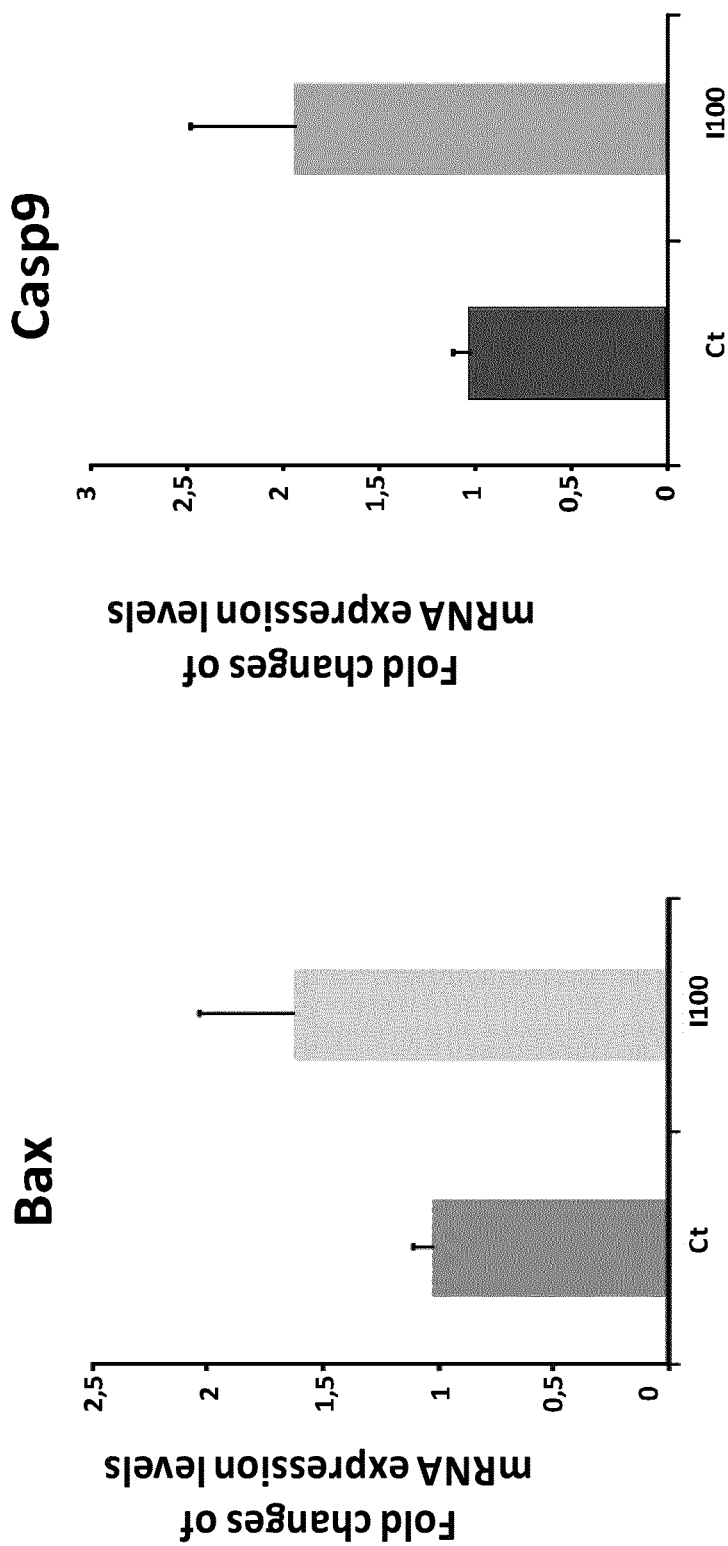
Figure 3:
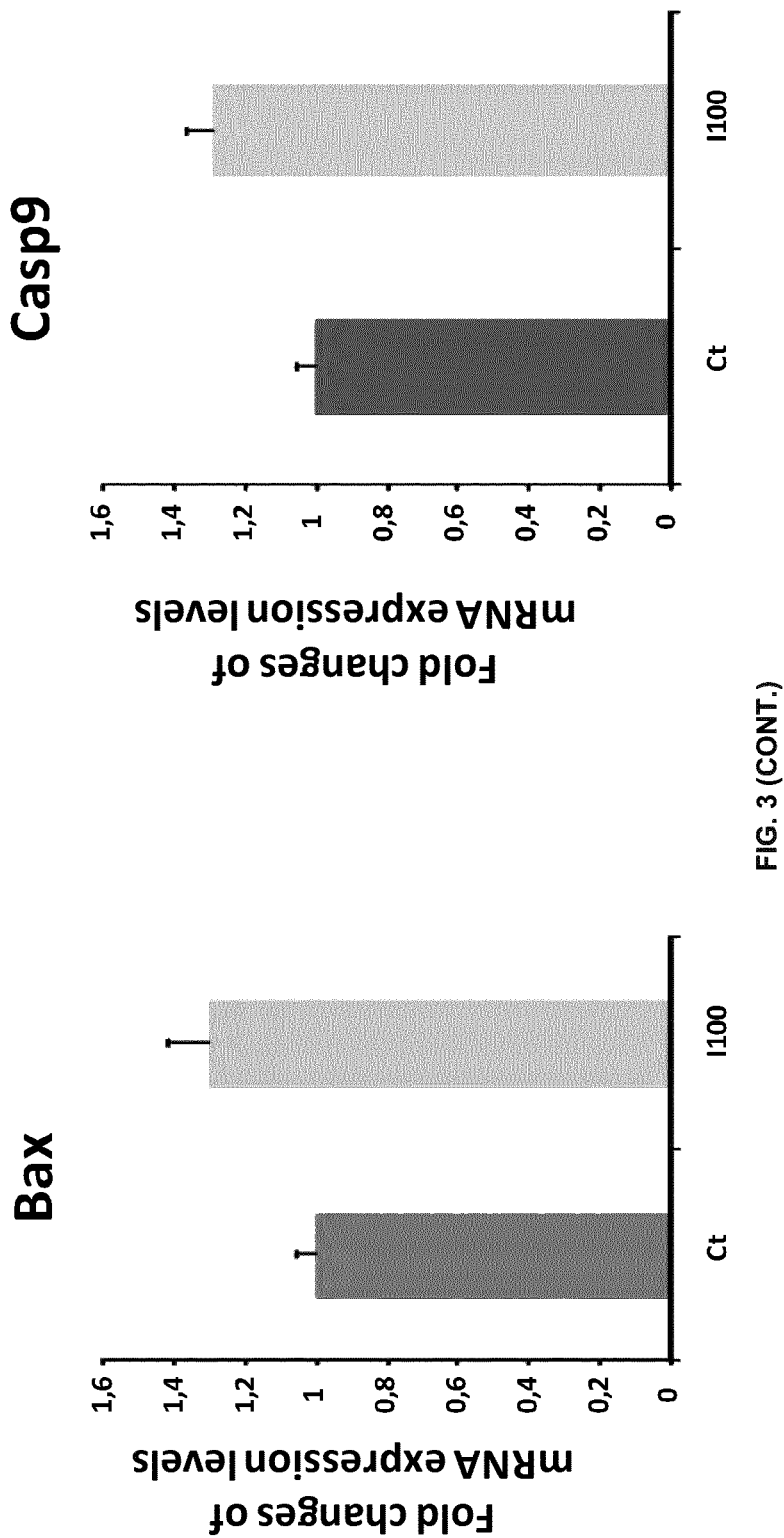

The inventors of the present invention have surprisingly found that ICI 118,551 decreases viability of hemangioblastoma cells from VHL patients (FIGS. 1 and 2) and inhibits hemangiosphere formation from VHL patients (FIG. 3). Additionally, the inventors have shown that ICI 118,551 inhibits cell migration and angiogenesis of endothelial cells (FIGS. 3 and 4) and that inhibits HIF activity induced by hypoxia.

Thus, the invention relates to a selective antagonist of the $\beta_2$-adrenergic receptor for use in the treatment and/or prevention of von Hippel-Lindau disease.

DETAILED DESCRIPTION OF THE FIGURES

FIG. 1. ICI 118,551 and Propranolol decrease viability of hemangioblastoma cells from VHL patients. Propranolol, (P) is a non-selective beta blocker binding beta 1 and 2 adrenergic receptors. ICI 118,551 (I), is a selective beta blocker binding only to receptor beta 2. Both beta-blockers act by decreasing viability of hemangioblastoma primary cell cultures up to 40%-50% at 100 µM for 72 hours. FIG. 1 shows the decrease in viability in primary cell culture HB11cib. Results are representative of 8 hemangioblastoma primary cell cultures treated in the same way. Each measure comes from triplicates, and quantified by a luminescent kit detecting ATP (Cell titer Glo, from Promega).

FIG. 2. ICI 118,551 acts as propranolol decreasing viability in hemangioblastoma cells from VHL. A. Hemangioblastoma cell primary culture (patient sample HB18), without (Control) and after 4 days of treatment with ICI 118,551 at 50 y 100 µM. After treatment with ICI 118,551 100 µM we can see empty spaces in the plate, compared with control, which is confluent after 4 days of culture, starting with the same number of cells. B. Comparison of 4-day treatment with Propranolol (P) and ICI 118,551 (I) at the same concentration 100 µM of hemangioblastoma cell primary culture (patient sample HB4).

FIG. 3. ICI 118,551 treatment induces cell apoptosis by stimulating proapoptotic genes Bax and Caspase 9 A. Relative mRNA expression levels of BAX and CASP9 (genes involved in apoptosis) detected by RT-qPCR in HB26 hemangioblastoma cell culture, after 72 h of 100 µM ICI 118,551 (1100). B. Relative mRNA expression levels of Bax and Casp9 (genes involved in apoptosis) detected by RT-qPCR in HB11 hemangioblastoma cell culture, after 72 h of 100 µM ICI 118,551. Both genes, Bax and Casp 9 are increased after ICI 118,551 treatment, therefore, ICI 118,551 is inducing apoptosis in these cells.

Figure 4:
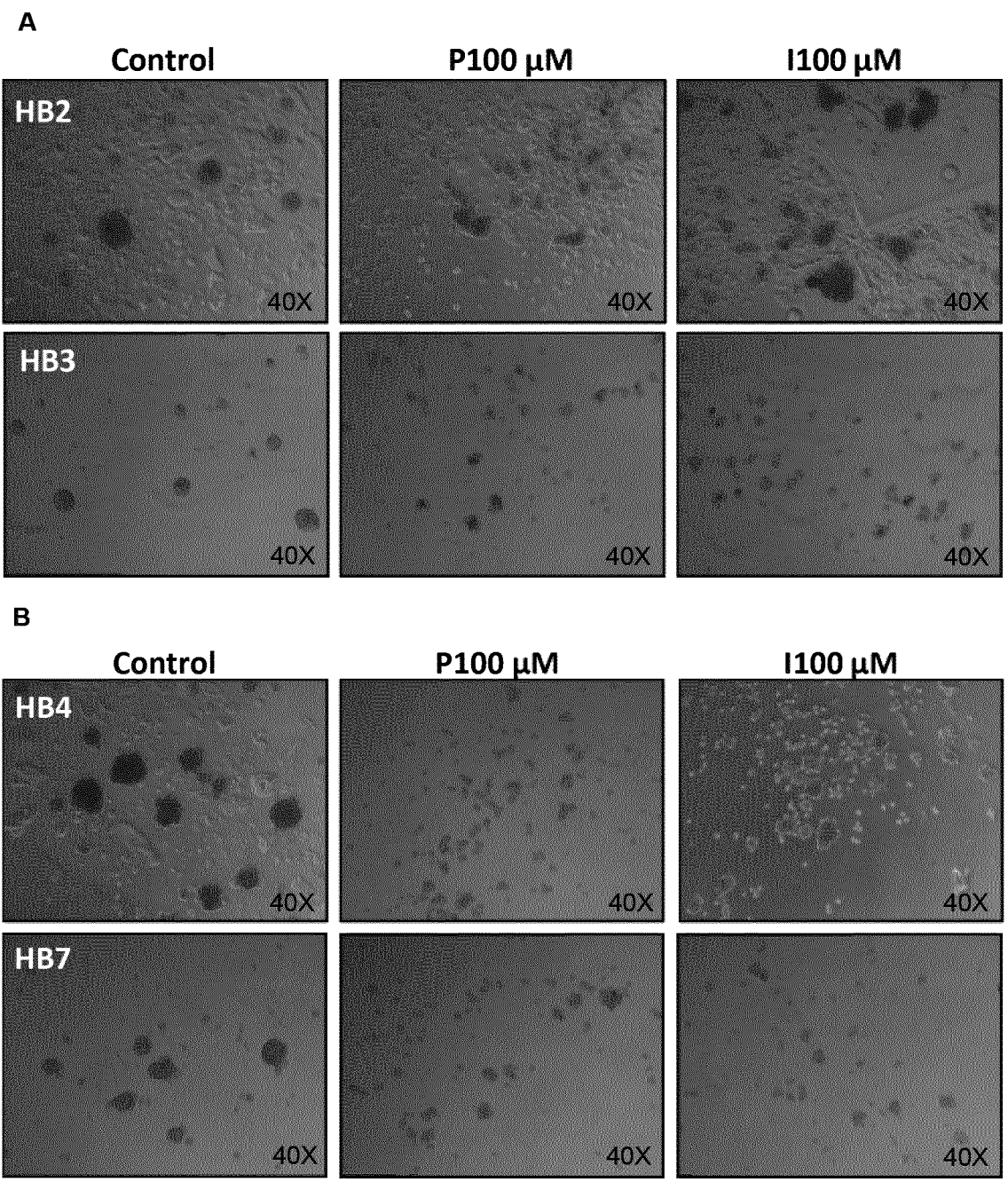
Figure 4:
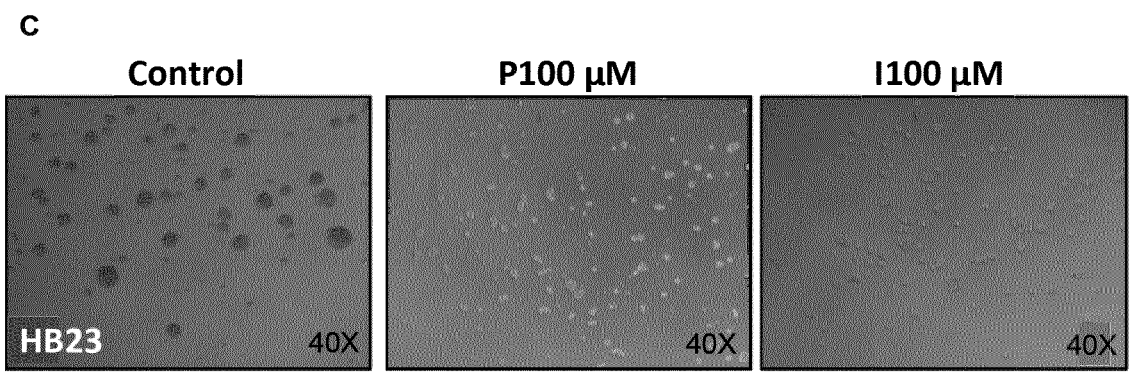

FIG. 4. Propanolol and ICI 118,551 are antitumoral agents, inhibiting hemangiosphere formation from VHL patient cells. A. Round sphere-like structures with a well-defined border appear as aggregates from of VHL cell tumors. Two different hemangioblastomas were used for these experiments HB2 and HB3. However, when the cells are cultured for 7 days in the presence of 100 µM of either, Propranolol (P) or ICI 118,551 (I), the spheres appear disaggregated and the observed groups are irregular with few cells. Photos were taken the last day of treatment B. The same as in panel A but with other two hemangioblastomas from VHL patients. C. The same as in panels A and B but with HB23 from a VHL patient.

Figure 5:
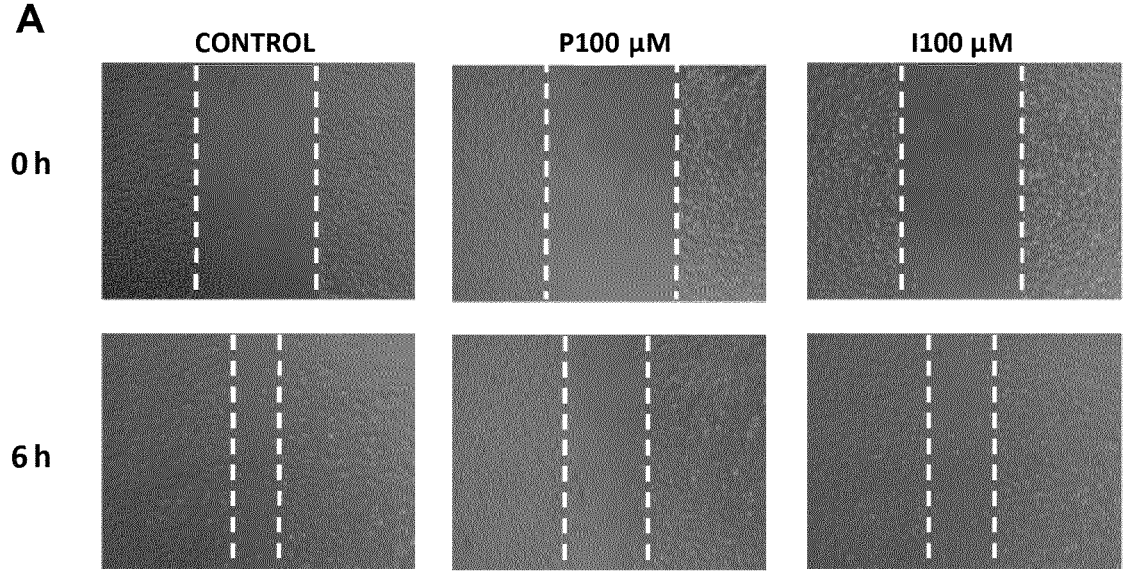
Figure 5:
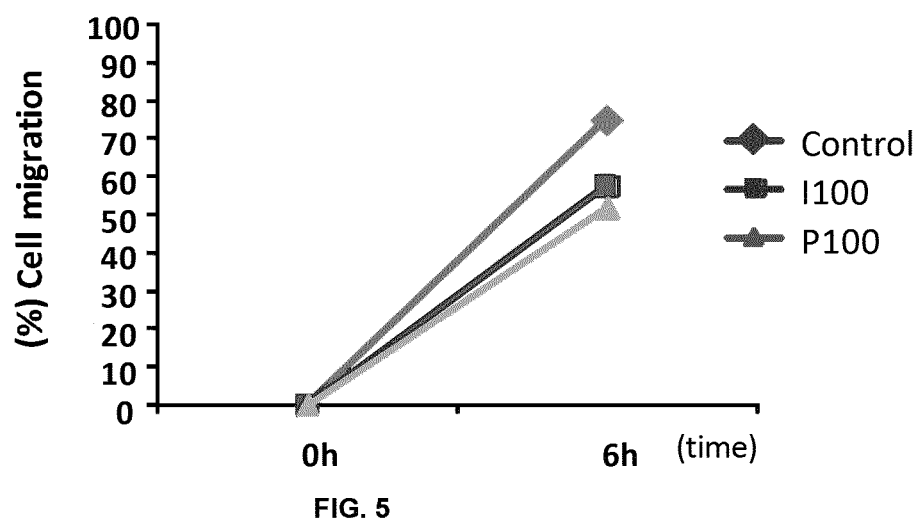

FIG. 5. ICI 118,551 and propranolol inhibit cell migration of endothelial cells. A. Functional in vitro tests for angiogenesis include "wound-healing" or plate-scratch, to follow the migration capacity of endothelial cells after short times. When a confluent monolayer is disrupted with the tip of a micropipette to create a discontinuity, endothelial cells normally migrate to cover the discontinuity "wound the healing" in a short time, depending on the size of the "wound" but normally, less than 8 hours. This test measures the migration by taking pictures at different times from the moment the wound is created. Only the final picture after 6 hours is shown. The migrated distance is quantified, and in the following graph the evolution is shown. ICI 118,551 and propranolol delay cell migration, hence they are antiangiogenic. B. Migrated distance by untreated and propranolol/ICI 118,551 treated-cells after 6 hours of making a scratch on the confluent layer of HUVECs (Human Umbilical Vein Endothelial Cells).

Figure 6:
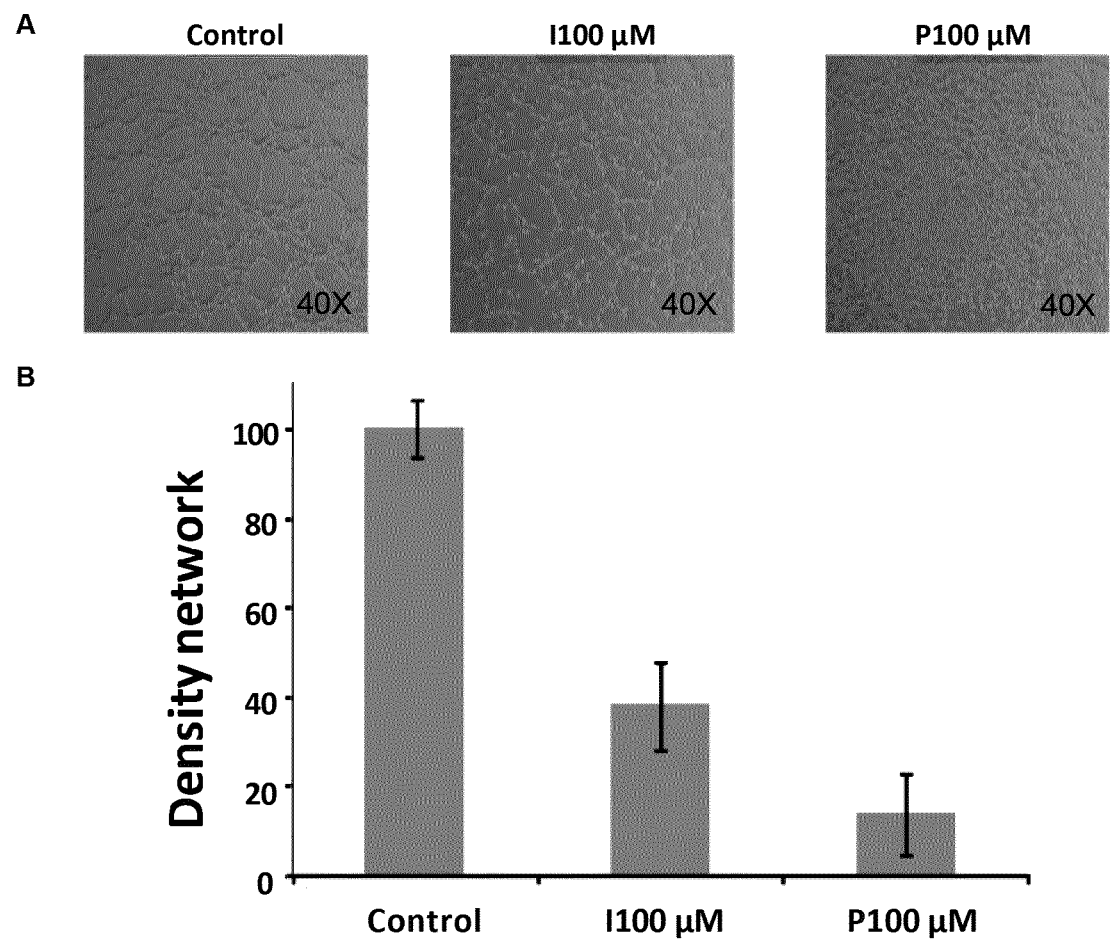

FIG. 6. ICI 118,551 and propranolol inhibit cell angiogenesis of endothelial cells. Tubulogenesis is another in vitro test for angiogenesis. Endothelial cells cultured on matrigel have the property of building cell tube-like structures, which mimic the "vessels" structure. A. Propranolol and ICI 118,551 at 100 µM significantly inhibit the tubulogenesis. B. The number of closed cells (density network) is quantified and averaged from 5 different fields in each case. Bar histograms represent the mean±SD.

Figure 7:
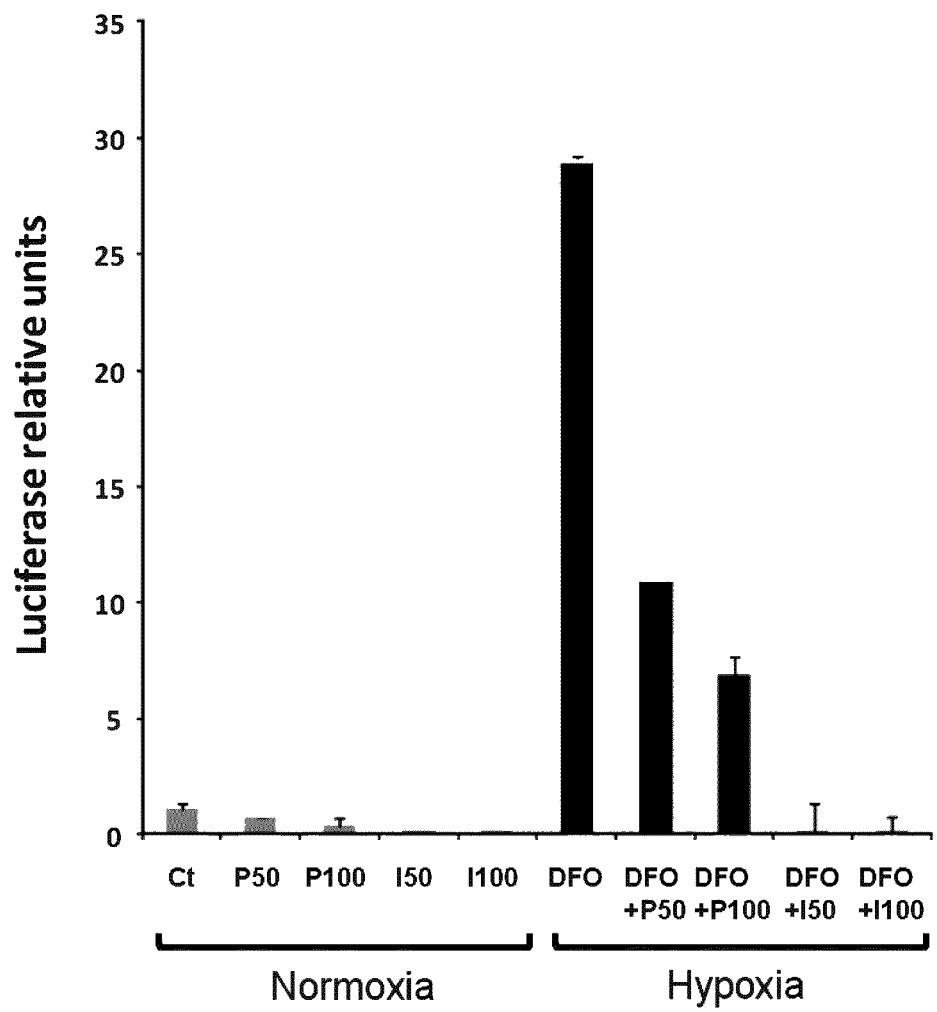

FIG. 7. Propranolol and ICI 118,551 inhibit HIF mediated stimulation. The bar histograms show the relative luciferase activity depending on HIF-1 (hypoxia) in stable transfectants of Hela cells for the reporter HRE9x-luc, that contains 9 tandem repetitions of the hypoxia responsive sequence element bound by HIF-1 fused with luciferase reporter protein. Ct stands for control cells (normoxia and hypoxia). Deferroxamin (DFO) at 100 µMolar produces chemical hypoxia in treated cells. Treatment with Propanolol or with ICI 118,551 at 50 or 100 µMolar (P50, P100, I50, I100, respectively, for 24 h), inhibits the hypoxia stimulation induced by DFO. Remarkably, the effect of ICI 118,551 is clearly superior to propranolol at equal dose. Both DFO and drug treatment were simultaneously administrated.

Figure 8:
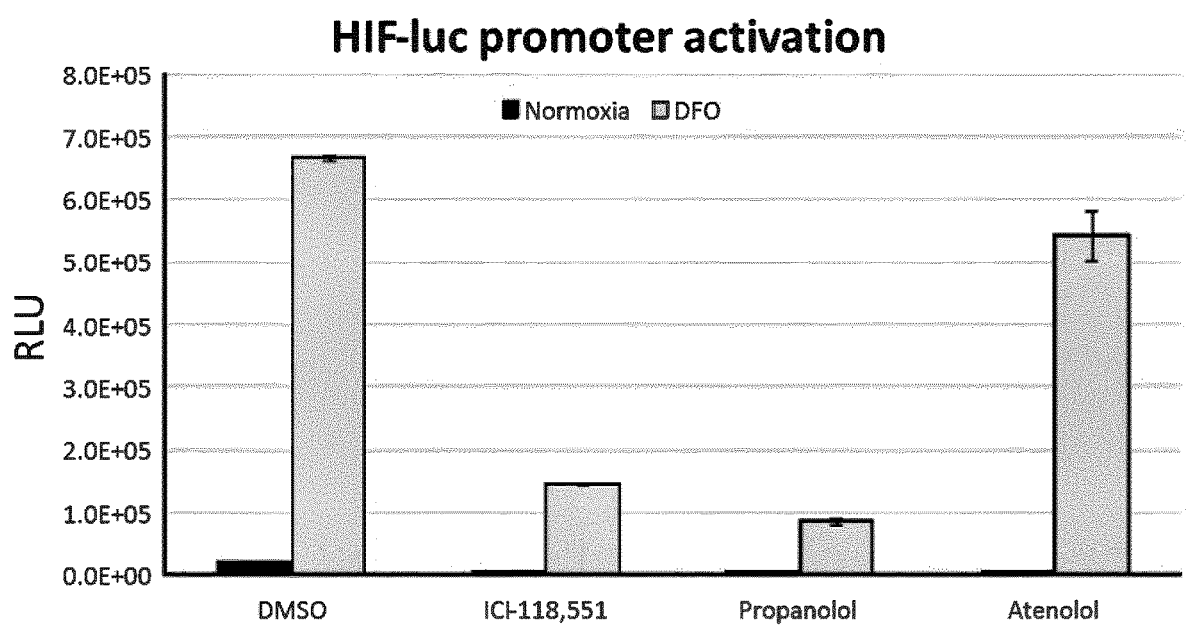

FIG. 8. Propranolol and ICI 118.551 downregulate significantly HIF-dependent transcription in HeLa cells but not Atenolol. Luciferase assays were performed in HRE-luc-stably transfected HeLa cells under hypoxic conditions and treatment with Propranolol, atenolol and ICI118.551. Propranolol and ICI (100 µM) prevented hypoxia stimulation in HeLa cells, as shown by the decrease in luciferase activity, by inhibiting the activation of hypoxia elements (HRE) by HIF. Atenolol results were less significant than the other ones (Propranolol and ICI).

Figure 9:
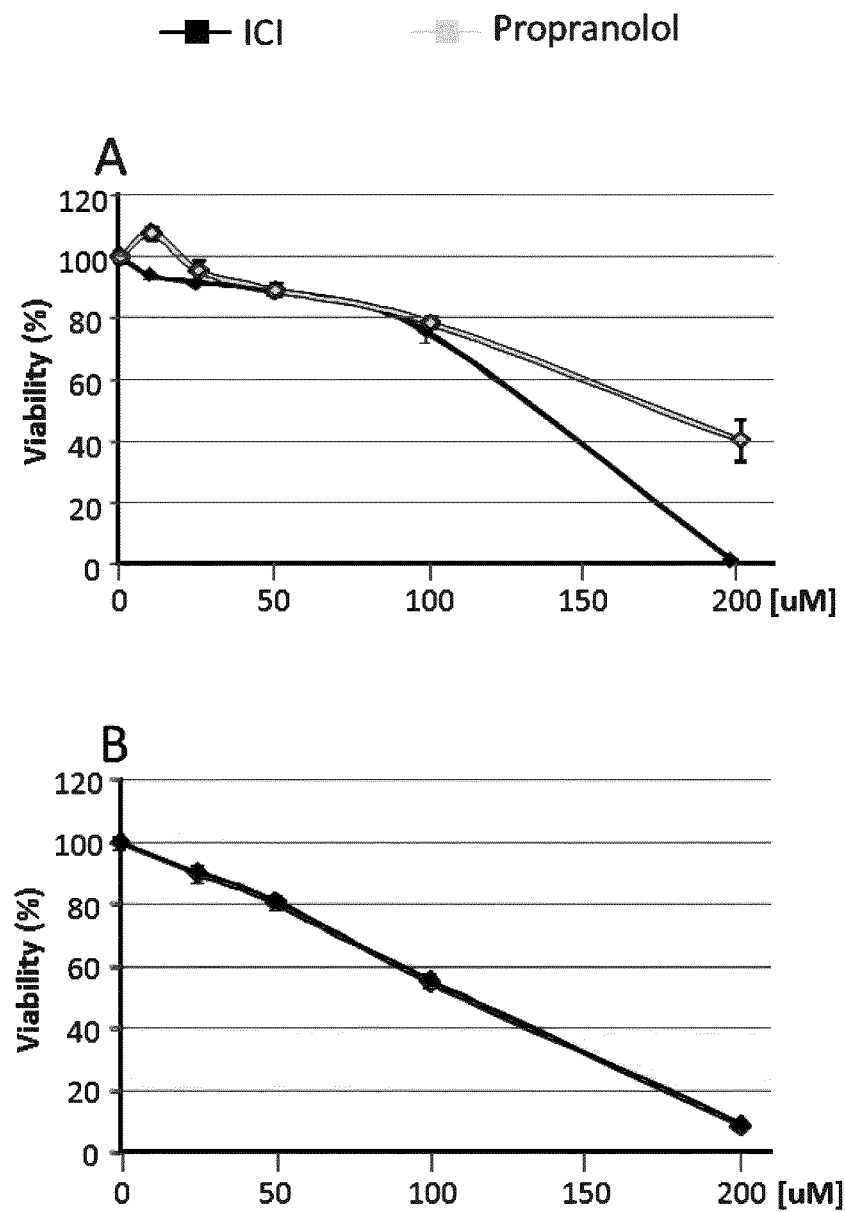
Figure 9:
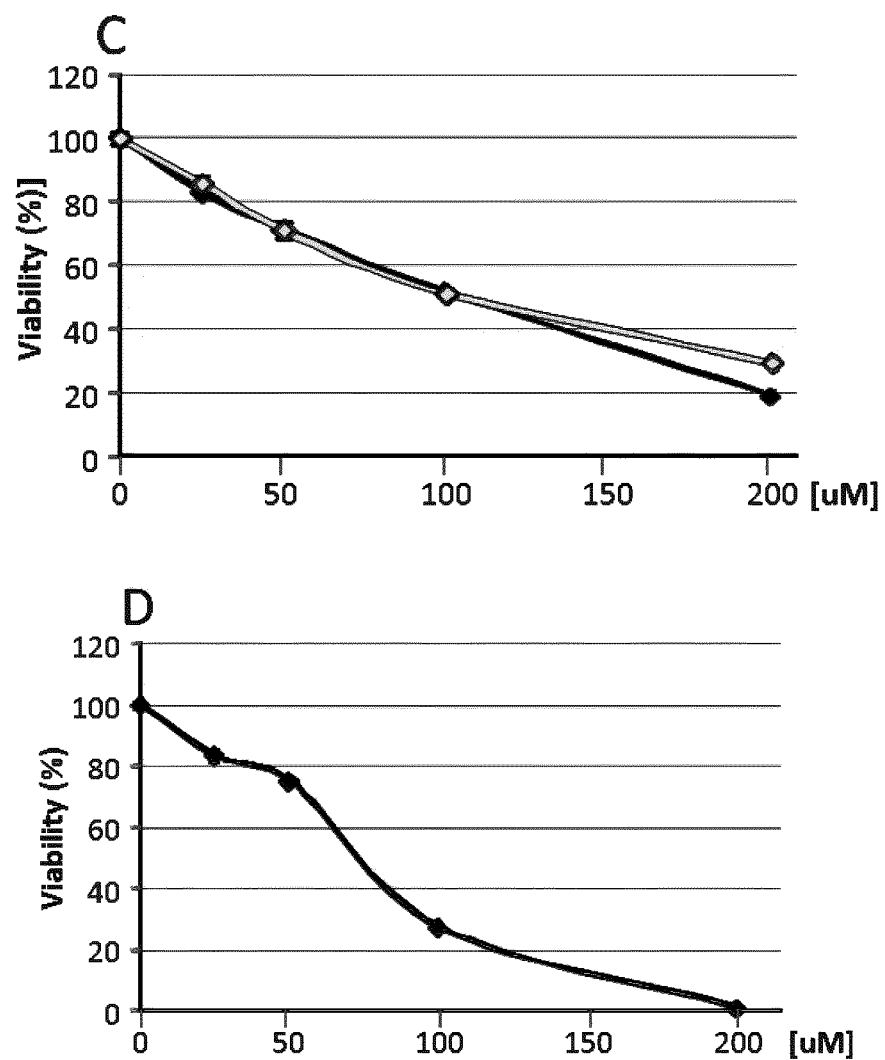
Figure 9:
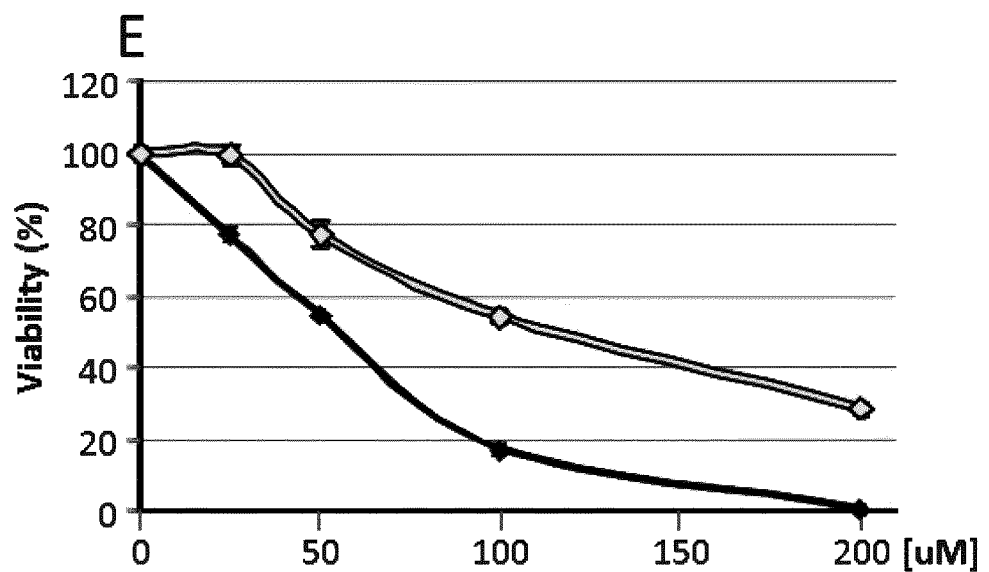

FIG. 9. ICI-118551 Shows antitumoral specific activity in VHL−/− cells. Viability (ATP content) of several cells (primary cultured and lines) exposed to different mM concentrations of ICI-118551 or Propranolol, for 72 hours. Control wells did not contain ICI-118551 or Propranolol. ICI-118551 (a specific beta-adrenergic receptors type 2 antagonist) and propranolol (a non-specific beta-adrenergic receptors type 1 and 2 antagonist) decrease, in a dose-dependent manner and with higher specificity, the viability of the VHL−/− cells. ATP content was measured using the CellTiter-Glo® Assay from Promega. A: HUVEC cell line, B: HMEC cell line, C: Hemangioblastoma primary culture 18, D: Hemangioblastoma primary culture 14, E: ccRCC Vhl−/− 786-O cell line. Data shown represent the mean+/− SEM (n=3).

Figure 10:
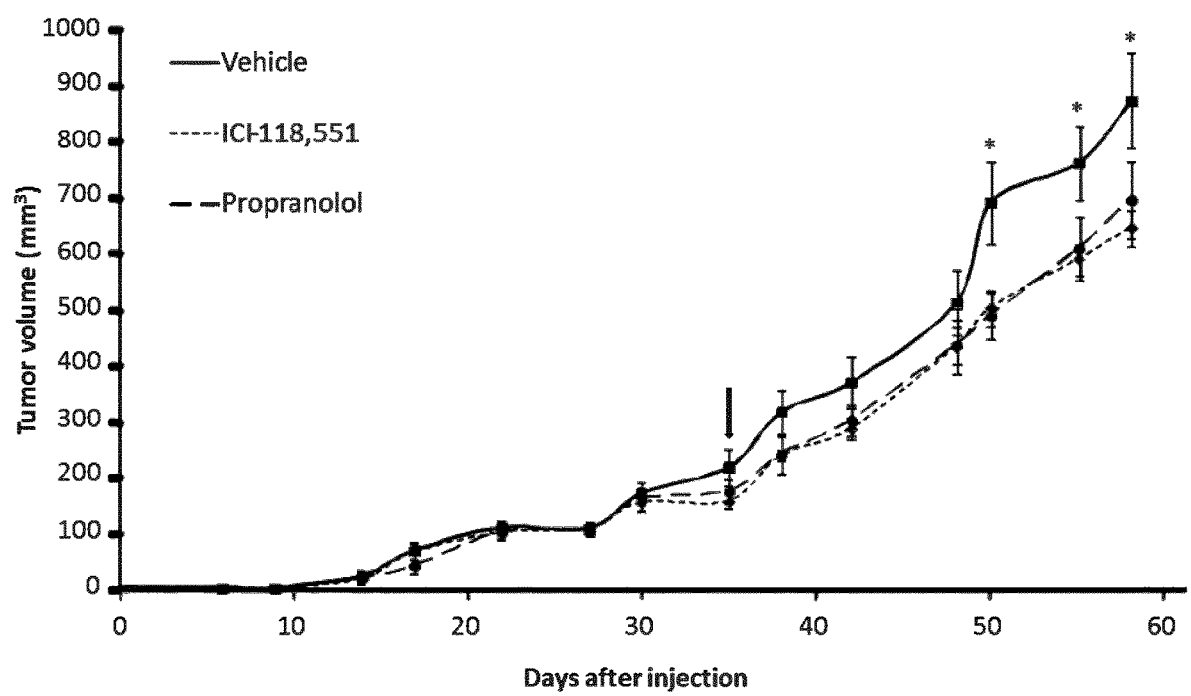

FIG. 10. Xenografts of 786-O Vhl−/− human ccRCC cells in mice. Male 7-8 weeks old NOD scid gamma (NSG) mice were injected in the dorsal flank with a single cell suspension of $10^6$ 786-O cells. When tumor size reached 100 mm3 volume, mice were randomly divided in 3 groups, of 9/10 mice each. Two groups were daily treated intraperitoneally with 10 mg/Kg body propranolol or ICI-118,551, respectively and a third group was injected with the solvent. Tumor size was measured by a caliper every 2-3 days and volumes were calculated following the formula: shortest$^2$×largest× 0.52. Mice were sacrificed when tumor volume average of the control group reached an end point established based on ethical procedures. Arrow marks the beginning of the treatment.

Figure 11:
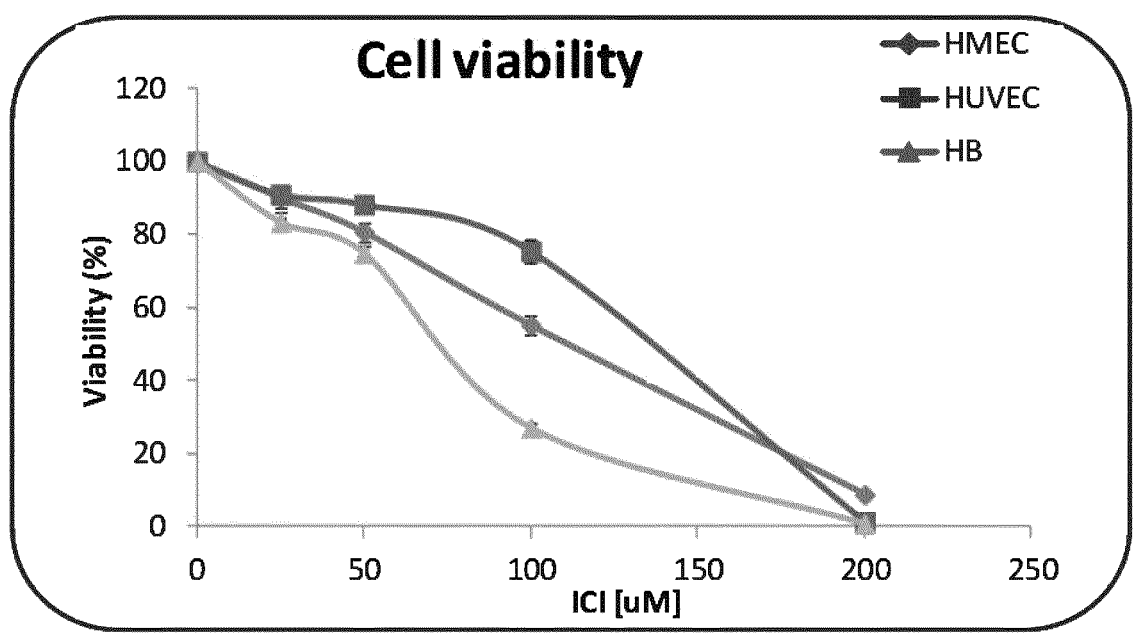

FIG. 11. ICI 118.551 affects differentially Vhl−/− cells and normal endothelial cells HUVECs and HMECs. Primary culture of Haemangioblastoma from VHL, normal primary endothelial HUVECs, and the non tumoral microendothelial cell line HMEC-1 were cultured in the absence or presence of different concentrations of ICI 118.551 (50-250 µM) to measure viability. According to viability curves Haemangioblastoma (HB) cells show only 20% of viability at 100 µM, while HUVEC or HMEC-1 non tumoral cells show 80% and 55% respectively decrease in viability at 100 µM in both cultures,

DETAILED DESCRIPTION OF THE INVENTION

The invention relates to a selective antagonist of the $\beta_2$-adrenergic receptor for use in the treatment and/or prevention of von Hippel-Lindau disease.

Alternatively, the invention relates to the use of a selective antagonist of the $\beta_2$-adrenergic receptor in the manufacture of a medicament for the treatment and/or prevention of von Hippel-Lindau disease.

Alternatively, the invention relates to a method of treatment and/or prevention of von Hippel-Lindau disease comprising administering to said patient a therapeutically effective amount of a selective antagonist of the $\beta_2$-adrenergic receptor.

The term "$\beta_2$-adrenergic receptor" or "β2AR", as used herein, refers to a class A of G protein-coupled receptors (GPCR) that responds to diffusible hormones and neurotransmitters and resides predominantly in smooth muscles. There are two main groups of adrenergic receptors, α and β, with several subtypes:
  α receptors have the subtypes $\alpha_1$ (a $G_q$ coupled receptor) and $\alpha_2$ (a $G_i$ coupled receptor).
  β receptors have the subtypes $\beta_1$, $\beta_2$ and $\beta_3$. All three are linked to $G_s$ proteins, which in turn are linked to adenylate cyclase. Agonist binding to these receptors causes a rise in the intracellular concentration of the second messenger cAMP.

Agonist binding to the $\beta_2$-adrenergic receptor results in smooth muscle relaxation.

The term "$\beta_2$-adrenergic receptor antagonist", as used herein, refers to a compound that binds a $\beta_2$-adrenergic receptor and lacks any substantial ability to activate the receptor itself. The term "$\beta_2$-adrenergic receptor antagonist" includes both neutral antagonists and inverse agonists. A "neutral antagonist" is a compound that blocks the action of the agonist but has no effect on intrinsic or spontaneous receptor activity. An "inverse agonist" is able to both block the action of the agonist at the receptor and attenuate the constitutive activity of the receptor. The term "antagonist" also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero.

The term "selective $\beta_2$-adrenergic receptor antagonist", as used herein, means an antagonist which is selective for $\beta_2$-adrenergic receptors over $\beta_1$-adrenergic receptors. In a particular embodiment, a selective $\beta_2$-adrenergic receptor antagonist exhibits at least 10-fold greater potency in binding to $\beta_2$- than to $\beta_1$-adrenergic receptors, i.e. have a $\beta_2/\beta_1$ selectivity ratio of at least 10. More preferably, the selective $\beta_2$ receptor antagonist will have a $\beta_2/\beta_1$ selectivity ratio of at least 50. The affinity of various active agents for $\beta_2$- and $\beta_1$-adrenergic receptors can be determined by evaluating tissues containing a majority of $\beta_2$ receptors (e.g., rabbit ciliary process, rat liver, cat choroid plexus or lung), tissues containing a majority of $\beta_1$ receptors (e.g., cat and guinea pig heart), and tissues containing a mixture (e.g. guinea pig trachea). The methods of determining relative binding selectivity for these different types of tissues are extensively disclosed in O'Donnell and Wanstall, Naunyn-Schmiedeberg's Arch. Pharmaco., 308, 183-190 (1979), Nathanson, Science. 204, 843-844 (1979), Nathanson, Life Sciences, 26, 1793-1799 (1980), Minneman et al., Mol. Pharmacol., 15, 21-33 (1979a), and Minneman et al., Journal of Pharmacology and Experimental Therapeutics, 211, 502-508 (1979).

A significant number of compounds having selective $\beta_2$-adrenergic antagonist activity suitable for use in this invention are known. In a particular embodiment, the selective $\beta_2$-adrenergic receptor antagonist is the alkanolamine derivative of formula I

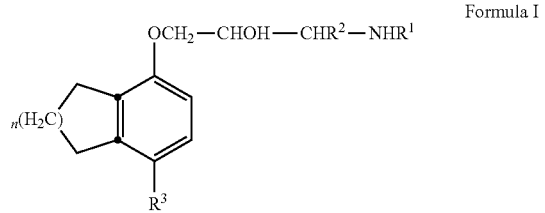

Formula I wherein $R^1$ is an alkyl group of up to 6 carbon atoms which is branched at the α-carbon atom,
wherein $R^2$ is an alkyl of up to 3 carbon atoms,
wherein $R^3$ is hydrogen, an halogen or an alkyl of up to three carbon atoms and
wherein n is 1 or 2,
or a pharmaceutically acceptable acid addition salt thereof.

The term "alkyl group", as used herein, refers to acyclic straight and branched groups derivable from alkanes, and having the formula —CnH2n+1 by removal of a hydrogen atom.

The term "halogen", as used herein, refers to an atom selected from fluorine, chlorine, bromine and iodine.

$R^1$ may be, for example, isopropyl or t-butyl. In a particular embodiment, $R^1$ is isopropyl.

$R^2$ may be, for example, methyl or ethyl. In a particular embodiment, $R^2$ is methyl.

$R^3$ may be, for example, hydrogen, chlorine, bromine, methyl or ethyl. In a particular embodiment, $R^3$ is methyl.

In a particular embodiment n is 1.

In a particular embodiment, $R^1$ is isopropyl and $R^2$ is methyl. In a particular embodiment, $R^1$ is isopropyl and R3 is methyl. In a particular embodiment, $R^1$ is isopropyl and n is 1. In a particular embodiment, $R^2$ is methyl and $R^3$ is methyl. In a particular embodiment, $R^2$ is methyl and n is 1. In a particular embodiment, $R^3$ is methyl and n is 1.

In a particular embodiment, $R^1$ is isopropyl and $R^2$ and $R^3$ are methyl. In another particular embodiment, $R^1$ is isopropyl, $R^2$ is methyl and n is 1. In another particular embodiment, $R^1$ is isopropyl, $R^3$ is methyl and n is 1. In a particular embodiment, $R^2$ and $R^3$ are methyl and n is 1.

In a more particular embodiment, $R^1$ is isopropyl, $R^2$ and/or $R^3$ are methyl and n is 1.

In an even more particular embodiment, the alkanolamine derivative has the formula II:

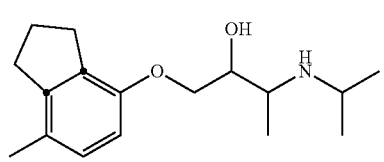

Formula II

This compound of formula II is also known as ICI 118,551 and its chemical name is erythro-D,L-1(methylinden-4-yloxy)-3-isopropylaminobutan-2-ol. ICI 118,551 has a $\beta_2/\beta_1$ selectivity ratio of at least 50, as determined and reported in Life Sciences, 27,671 (1980) and Bilsky et al., J. Cardiovasc. Pharmacol., 5, 430-437 (1983).

It will be observed that the alkanolamine derivative of formula I possesses two asymmetric carbon atoms, namely those of the —CHOH— group and the —CHR2— group, and that it can therefore exist in two racemic diastereoisomeric forms, the threo and erythro forms, and four optically-active forms, those being the (+) and (−) isomers of each of the racemic forms. It is to be understood that this invention encompasses any one of these isomeric forms which possess a selective $\beta_2$-adrenergic receptor antagonistic activity as defined above, it being a matter of common general knowledge how any particular isomer may be isolated and how any selective $\beta_2$-adrenergic receptor blocking activity it may possess may be measured.

It is to be understood that in general an optical isomer which has the {S}-absolute configuration of the —CHOH— group is more active as a $\beta_2$ adrenergic blocking agent than the corresponding isomer which has the {R}-absolute configuration. It is also known that in general the erythro-isomer is more $\beta_2$-selective than the corresponding threo-isomer, but that both threo- and erythro isomers of the compounds of the present invention possess the required selectivity.

The term "pharmaceutically acceptable acid-addition salt" refers to any acid-addition salt, which, upon administration to the recipient is capable of providing (directly or indirectly) a compound as described herein. Preferably, as used herein, the term "pharmaceutically acceptable salt" means approved by a regulatory agency of the Federal or a state government or listed in the U.S. Pharmacopeia or other generally recognized pharmacopeia for use in animals, and more particularly in humans. The preparation of salts can be carried out by methods known in the art. Illustrative non-limitative examples of pharmaceutically-acceptable acid-addition salt of the alkanolamine derivative of formula I is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis(2-hydroxy-3-naphthoate), or a salt derived from an acidic synthetic resin, for example a sulphonated polystyrene resin. In a particular embodiment, the pharmaceutically acceptable acid-addition salt is hydrochloride. In a more particular embodiment, the selective antagonist of the $\beta_2$ adrenergic receptor antagonist is the hydrochloride salt of the compound of formula II.

In another particular embodiment, the selective $\beta_2$-adrenergic receptor antagonist is selected from a list comprising the following compounds:

Butoxamine

The chemical name for butoxamine is DL-erythro-α-(2,5-dimethoxyphenyl)-β-t-butyl aminopropanol hydrochloride. Determination of the Beta$_2$ selectivity of butoxamine is reported in O'Donnell and Wanstall, Naunyn-Schmiedeberg's Arch. Pharmaco., 308, 183-190 (1979), which reports a $\beta_2/\beta_1$ selectivity ratio of at least 17.

H35/25

The chemical name for H35/25 is 1-(4'-methylphenyl)-b 2,2-I-isopropylaminopropanol.

Prenalterol

Prenalterol is a compound of formula

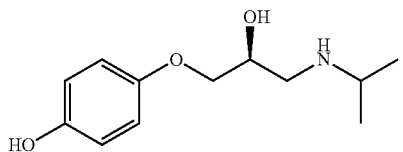 [SMILES: CC(C)NC[C@H](O)COc1ccc(O)cc1]

The selective $\beta_2$-adrenergic receptor antagonistic activity is described by Johansson and Waldeck, J. Pharm. Pharmacol., 1988, 32(9), 659-660.

Various 4- and 5-[2-hydroxy-3-(isopropylamino) propoxy]benzimidazoles as described by Crooks et al, J. Med. Chem., 22(2), 210-214 (1979).

1-(t-butyl-amino-3-ol-2-propyl)oximino-9 fluorene, as described by Imbs et al, Br. J. Pharmacol. 60(3), 357-362 (1977).

Various 2-(alpha-hydroxyarylmethyl)-3,3-dimethylaziridines as described by Jain et al, J. Med. Chem., 21(1), 68-72 (1978).

The term "treatment", as used herein, refers to any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "prevention", as used herein, refers to the administration of a compound of the invention in an initial or early stage of the disease, or to also prevent its onset.

The term "von Hippel-Lindau disease" or "VHL disease" or "von Hippel-Lindau disease" or "VHL disease" or "VHL syndrome" or "von Hippel-Lindau syndrome", as used herein, refers to a rare disease caused by a mutation in the von Hippel-Lindau (VHL) tumor suppressor leading to an absence of VHL protein or to an aberrant non-functional VHL protein. More than 370 inherited mutations in the VHL gene have been identified in people with von Hippel-Lindau disease (http://www.umd.be/VHL/). VHL gene mutations associated with this condition either prevent the production of any VHL protein or lead to the production of an abnormal version of the protein. VHL disease is characterized by the formation of multiple benign and malignant tumors and fluid-filled sacs (cysts) in many different parts of the body, including: retinal hemangioblastoma, CNS hemangioblastoma, clear cell renal cell carcinoma (CCRCC), pheochromocytoma, pancreatic islet tumor, endolymphatic sac tumors and cysts in testes and broad ligament.

The term "patient" or "subject", as used herein, refers to any animal, preferably a mammal and includes, but is not limited to, domestic and farm animals, primates and humans, for example, human beings, non-human primates, cows, horses, pigs, sheep, goats, dogs, cats, or rodents. In a preferred embodiment, the subject is a human being of any age or race. In the present invention, the patient suffers from von Hippel-Lindau disease.

The term "patient with von Hippel-Lindau disease", as used herein, means that the patient has been diagnosed with the VHL disease. VHL disease can be diagnosed according with the following diagnostic criteria (Frantzen et al, Von Hippel-Lindau Syndrome, GeneReviews®):

For an individual with no family history of VHL disease,
VHL disease is diagnosed if the patient presents two or more characteristic lesions:
Two or more hemangioblastomas of the retina, spine, or brain or a single hemangioblastoma in association with a visceral manifestation (e.g., multiple kidney or pancreatic cysts).
Renal cell carcinoma.
Adrenal or extra-adrenal pheochromocytomas.
Less commonly, endolymphatic sac tumors, papillary cystadenomas of the epididymis or broad ligament, or neuroendocrine tumors of the pancreas.
For an individual with a positive history of VHL disease,
VHL disease is diagnosed if one or more of the following disease manifestations is present:
Retinal angioma
Spinal or cerebellar hemangioblastoma
Adrenal or extra-adrenal pheochromocytoma
Renal cell carcinoma
Multiple renal and pancreatic cysts
In any case where a heterozygous germline VHL pathogenic variant is identified by molecular testing.
In a particular embodiment, the VHL disease occurs with the appearance of one or more tumors.

In a particular embodiment, the invention relates to a selective antagonist of the $\beta_2$-adrenergic receptor for use in the treatment and/or prevention of a tumor in a patient with von Hippel-Lindau disease.

The term "tumor" or "cancer", as used herein, refers to a broad group of diseases involving unregulated cell growth and which are also referred to as malignant neoplasms. The term is usually applied to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. In a particular embodiment, the cancer appears as a benign tumor, i.e. tumors that cannot spread by invasion or metastasis, i.e., they only grow locally. In another particular embodiment, the cancer appears as a malign tumor, i.e. a tumor that is capable of spreading by invasion and metastasis.

Illustrative non-limitative examples of tumors are hemangioblastoma, pheochromocytoma, endolymphatic sac tumor, lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, cyst in the broad ligamentum, peritoneum, omentum, and mesentery cancer, pharynx cancer, prostate cancer, rectal cancer, renal cancer, including renal cell carcinoma, skin cancer, soft tissue cancer, testicular cancer, cysts in testes, thyroid cancer, ureter cancer, urinary bladder cancer, and digestive tract cancer such as, e.g., esophageal cancer, gastric cancer, pancreatic cancer, including pancreatic islet tumor, stomach cancer, small intestine cancer, gastrointestinal carcinoid tumor, cancer of the oral cavity, colorectal cancer, and hepatobiliary cancer.

In a particular embodiment, the tumor is not a pancreatic tumor. The term "pancreatic tumor", as used herein, includes both exocrine and endocrine tumors. Exocrine tumors in pancreas include adenocarcinoma, acinar cell carcinoma, intraductal papillary-mucinous neoplasm (IPMN), mucinous cystadenocarcinoma among others. Endocrine tumors in the pancreas, also called "islet cell tumors" include gastrinoma (Zollinger-Ellison syndrome), glucagoma, insulinoma, somastostatinoma, VIPoma (Verner-Morrison syndrome), nonfunctional islet cell tumor and multiple endrocrine neoplasia type-1 (MEN1) among others. In a more particular embodiment, the tumor is not an exocrine pancreatic tumor. In an even more particular embodiment, the tumor is not a pancreatic adenocarcinoma.

In another particular embodiment, the tumor is selected from hemangioblastoma, clear cell renal cell carcinoma (CCRCC), pheochromocytoma, pancreatic islet tumor, endolymphatic sac tumors and cysts in testes and broad ligament.

The term "hemangioblastoma", as used herein, refers to a benign, highly vascular tumor that can occur in the central nervous system (brain or spinal cord) and in the retina. In a more particular embodiment, the tumor is hemangioblastoma. In an even more particular embodiment, the tumor is a retinal hemangioblastoma or a central nervous system hemangioblastoma.

The term "clear cell renal cell carcinoma" or "ccRCC", as used herein, refers to a renal cortical tumor typically characterized by malignant epithelial cells with clear cytoplasm and a compact-alveolar or acinar growth pattern with arborizing vasculature.

The term "pheochromocytoma" or "PCC", as used herein, refers to a neuroendrocrine tumor of the medulla of the adrenal glands, or extra-adrenal chromaffin tissue that filed to involute after birth, that secretes high amounts of catecholamines, mostly norepinephrine and, to a lesser extent, epinephrine.

The term "endolymphatic sac tumor", as used herein, refers to a papillary epithelial neoplasm arising within the endolymphatic sac or endolymphatic duct.

The term "cyst", as used herein, refers to a cluster of cells that have grouped together to form a sac. The distinguishing aspect of a cyst is that the cells forming the "shell" of such a sac are distinctly abnormal (in both appearance and behavior) when compared with all surrounding cells for that given location. It may contain air, fluids, or semi-solid material. In a particular embodiment, the cysts affect the testes or the broad ligament.

For its administration to the patient, the selective $\beta_2$ adrenergic receptor antagonist of the invention, preferably the alkanolamine derivative of formula I, more preferably the alkanolamine derivative of formula II, or a pharmaceutically acceptable acid-addition salt thereof, will be formulated in a pharmaceutical composition.

The term "pharmaceutical composition", as used herein, refers to a composition comprising a therapeutically effective amount of the selective $\beta_2$ adrenergic receptor antagonist of the invention, preferably the alkanolamine derivative of formula I, more preferably the alkanolamine derivative of formula II, or a pharmaceutically acceptable acid-addition salt thereof, and at least a pharmaceutically acceptable excipient or carrier.

The term "therapeutically effective amount", as used herein, refers to the sufficient amount of the compound to provide the desired effect and will generally be determined by, among other causes, the characteristics of the compound itself and the therapeutic effect to be achieved. It will also depend on the subject to be treated, the severity of the disease suffered by said subject, the chosen dosage form, administration route, etc.

For this reason, the doses mentioned in this invention must be considered only as guides for the person skilled in the art, who must adjust the doses depending on the aforementioned variables.

Even though individual needs vary, determination of optimal ranges for therapeutically effective amounts of the compounds for use according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs. The amount of the compound for use according to the invention that is therapeutically effective in the prevention and/or treatment of ischemia/reperfusion injury in a subject can be determined by conventional clinical techniques (see, for example, The Physician's Desk Reference, Medical Economics Company, Inc., Oradell, N J, 1995, and Drug Facts and Comparisons, Inc., St. Louis, Mo., 1993).

In a particular embodiment, the therapeutically effective amount produces the amelioration of one or more symptoms of VHL disease. In a particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose from about 0.2 mg/kg/day to about 5 mg/kg/day, preferably from about 0.5 mg/kg/day, about 0.7 mg/kg/day, about 1 mg/kg/day, about 1.5 mg/kg/day about 1.7 mg/kg/day, about 1.9 mg/kg/day, about 2.1 mg/kg/day, about 2.2 mg/kg/day, about 2.5 mg/kg/day, about 2.7 mg/kg/day, about 2.9 mg/kg/day, about 3.1 mg/kg/day, about 3.3 mg/kg/day, to about 4.9 mg/kg/day, about 4.8 mg/kg/day, about 4.7 mg/kg/day, about 4.6 mg/kg/day, about 4.5 mg/kg/day. In a more particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose between 3.3 mg/kg body/day and 4.5 mg/kg body/day. In another more particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose between 0.5 mg/kg body/day and 1 mg/kg body/day. In an even more particular embodiment, the selective $\beta_2$ adrenergic receptor antagonist, preferably the alkanolamine derivative of formula I, more preferably the alkanolamine derivative of formula II, or the pharmaceutically acceptable acid-addition salt thereof, is administered at a dose of 0.81 mg/kg body/day.

Doses of the compounds of the invention may be expressed either in mg of the antagonist per kg of body weight or in mg of the antagonist per square meter of body surface. The skilled person knows how to determine the dose for a particular animal, in particular the dose for human beings, from the doses experimentally assayed in mice. For example, the article from Reagan-Shaw S. et al. (Reagan-Shaw S. et al. "Dose translation from animal to human studies revisited". FASEB J 2008, 22(3):659-661) provides the standard conversion factors used to convert mg/kg to mg/m².

$$\text{Dose (mg/kg)} \times K_m = \text{Dose (mg/m}^2\text{)}$$

The article also explains that this conversion is the basis for converting dose in a first animal species to dose in a second animal species (allometric dose translation). Thus, animal dose (AD) in mg/kg can be converted to human equivalent dose (HED) in mg/kg using the following formula:

$$HED(mg/kg) = AD(mg/kg) \times \frac{\text{Animal } K_m}{\text{Human } K_m}$$

wherein the $K_m$ for each species is shown in Table 1 (data extracted from Reagan-Shaw S. et al. "Dose translation from animal to human studies revisited". FASEB J 2008, 22(3): 659-661).

TABLE 1

| $K_m$ factor for conversion of AD to HED | | |
|---|---|---|
| Species | | $K_m$ factor |
| Human | Adult | 37 |
|  | Child | 25 |
| Baboon |  | 20 |
| Dog |  | 20 |
| Monkey |  | 12 |
| Rabbit |  | 12 |
| Guinea pig |  | 8 |
| Rat |  | 6 |
| Hamster |  | 5 |
| Mouse |  | 3 |

Thus, the experiments with doses of 10 mg/kg in mice correspond to general doses in humans of 0.8 mg/kg.

In another particular embodiment, the selective $\beta^2$ adrenergic receptor antagonist, preferably the alkanolamine derivative of formula I, more preferably the alkanolamine derivative of formula II, or the pharmaceutically acceptable acid-addition salt thereof, is administered in humans, at a dose wherein each administration ranges from 0.2 mg/m² to 5 mg/m². preferably from about 0.2 mg/kg/day, about 0.25 mg/kg/day, about 0.3 mg/kg/day, about 0.35 mg/kg/day, about 0.4 mg/kg/day, about 0.45 mg/kg/day, about 0.50 mg/kg/day, about 0.55 mg/kg/day, about 0.6 mg/kg/day, about 0.65 mg/kg/day, about 0.7 mg/kg/day, about 0.75 mg/kg/day, about 0.8 mg/kg/day, about 0.85 mg/kg/day, about 0.90 mg/kg/day, about 0.95 mg/kg/day, about 1 mg/kg/day, about 1.2 mg/kg/day, about 1.4 mg/kg/day, about 1.6 mg/kg/day, about 1.8 mg/kg/day, about 2 mg/kg/day about 2.2 mg/kg/day, about 2.4 mg/kg/day, about 2.6 mg/kg/day, about 2.8 mg/kg/day, about 3 mg/kg/day, about 3.2 mg/kg/day, to about 3.4 mg/kg/day, about 3.6 mg/kg/day, about 3.8 mg/kg/day, about 4 mg/kg/day, about 4.5 mg/kg/day, about 5 mg/kg/day. In a more preferred embodiment, the selective β2 adrenergic receptor antagonist, preferably the alkanolamine derivative of formula I, more preferably the alkanolamine derivative of formula II, or the pharmaceutically acceptable acid-addition salt thereof, is administered at a dose between 0.7 mg/kg body/day and 1 mg/kg body/day. In a still more preferred embodiment, the selective β2 adrenergic receptor antagonist, preferably the alkanolamine derivative of formula I, more preferably the alkanolamine derivative of formula II, or the pharmaceutically acceptable acid-addition salt thereof, is administered at a dose of 0.81 mg/kg body/day.

In another particular embodiment, the selective $\beta^2$ adrenergic receptor antagonist, preferably the alkanolamine derivative of formula I, more preferably the alkanolamine derivative of formula II, or the pharmaceutically acceptable acid-addition salt thereof, is administered daily preferably 1 time a day, 2 times a day, 3 times a day. In a more preferred embodiment, it is administered 1 time a day. In another particular embodiment, the selective β2 adrenergic receptor antagonist, preferably the alkanolamine derivative of formula I, more preferably the alkanolamine derivative of formula II, or the pharmaceutically acceptable acid-addition salt thereof, is administered during 10 days, 15 days, 20 days, 25 days, 1 month, 2 months, 3 months, 4 months, 5 months, 6 months, 7 months, 8 months, 9 months, 10 months, 11 months, 12 months or more than 12 months, preferably during 25 days.

The terms "pharmaceutically acceptable excipient" or "pharmaceutically acceptable carrier", refer to any compound or combination of compounds that is essentially non-toxic to the subject at the dosage and concentration employed, and is compatible with the other components of a pharmaceutical composition. Thus, an excipient is an inactive substance formulated alongside the active ingredient (i.e., the selective $\beta_2$ adrenergic receptor antagonist, preferably the alkanolamine derivative of formula I, more preferably the alkanolamine derivative of formula II, or the pharmaceutically acceptable acid-addition salt thereof) of a pharmaceutical composition, for the purpose of bulking-up compositions that contain said active ingredients. Bulking up allows convenient and accurate dispensation of a drug substance when producing a dosage form. Excipients also can serve various therapeutic enhancing purposes, such as facilitating compound (drug) absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients depends upon the rout of administration and the dosage form, as well as the active ingredient and other factors. An excipient can be a non-toxic solid, semisolid or liquid filler, diluent, encapsulating material or formulation auxiliary of any conventional type. Illustrative, non-limitative, examples of excipients or carriers include water, salt (saline) solutions, alcohol, dextrose, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

The selective $\beta_2$ adrenergic receptor antagonist of the invention, preferably the alkanolamine derivative of formula I, more preferably the alkanolamine derivative of formula II, or a pharmaceutically acceptable acid-addition salt thereof, may be administered by any suitable administration route, such as, but not limited to, parenteral, oral, topical, nasal, rectal, intravitreal route. In a particular embodiment, the selective $\beta_2$ adrenergic receptor antagonist of the invention, preferably the alkanolamine derivative of formula I, more preferably the alkanolamine derivative of formula II, or a pharmaceutically acceptable acid-addition salt thereof, is administered intraperitoneally, intravenously, subcutaneously, intradermically, intramuscularly or intravitreal. In a preferred embodiment, the selective $\beta_2$ adrenergic receptor antagonist of the invention, preferably the alkanolamine derivative of formula I, more preferably the alkanolamine derivative of formula II, or pharmaceutically acceptable acid-addition salt thereof, is administered orally or intravenously or intravitreal. In a more preferred embodiment, the selective β2 adrenergic receptor antagonist of the invention, preferably the alkanolamine derivative of formula I, more preferably the alkanolamine derivative of formula II, or pharmaceutically acceptable acid-addition salt thereof, is administered intraperitoneally.

The invention is described below by way of the following examples, which are to be seen as merely illustrative and not limitative of the scope of the invention.

EXAMPLES

Methods
Cell Culture

HeLa 9XHRE cells were stably transfected with a HREluc reporter carrying nine copies in tandem of the hypoxia responsive element (HRE) followed by luciferase gene, and were cultured in DMEM (Dulbecco's Modified Eagle Medium, Gibco, Grand Island, N.Y., USA) supplemented with 10% fetal bovine serum (FBS; Gibco). To induce hypoxic conditions, HeLa cells were cultured with 100 μM desferrioxamine (DFO) (chemical hypoxia). When required, HeLa cells were treated with Propranolol (non-selective beta blocker which binds both Beta 1 and Beta 2 receptors), ICI 118.551 (specific of Beta 2) and Atenolol (specific for Beta 1) (100 μM). Primary cultures of CNS hemangioblastoma were obtained according to the previously described by Albiñana et al., Orphanet J Rare Diseases, 2015, 10: 118. When required, primary cultures of CNS hemangioblastoma were treated with propranolol and ICI (100 μM).

Real-Time RT-PCR

Total cellular RNA was extracted from hemangioblastoma cells using a Nucleo Spin RNA kit (Macherey-Nagel, Düren, Germany). One microgram of total RNA was reverse-transcribed in a final volume of 20 μl with the First Strand cDNA Synthesis Kit (Roche, Mannheim, Germany) using random primers. SYBR Green PCR system (BioRad, Hercules, Calif., USA) was used to carry out real-time PCR with an iQ5 system. Primers used for qPCR were:

TABLE 2

Primers used for qPCR

| GENE | Forward | Reverse |
| --- | --- | --- |
| 18S | 5'-CTCAACACGGGAA ACCTCAC-3' | 5'-CGCTCCACCAACT AAGAACG-3'. |
| BAX | 5'-CACTCCCGCCACA AAGAT-3' | 5'-CAAGACCAGGGTG GTTGG-3' |
| CASP9 | 5'-CCCAAGCTCTTTT TCATCCA-3' | 5'-TTACTGCCAGGGG ACTCGT-3' |

Luminescent Cell Viability Assay

The viability of hemangioblastoma and HeLa 9XHRE cells was measured with a CellTiter-Glo Luminescent Cell Viability Assay (Promega, Madison, Wis., USA). This is a homogeneous method to determine the number of viable cells in culture based on quantitation of the ATP present, which signals the presence of metabolically active cells. A total of 10,000 cells were plated in 96-well plates and cultured with propranolol/ICI118,551 in 100 μl of medium. After treatment, plates were equilibrated to room temperature for 30 min before the addition of 100 μl of Cell Titer-Glo reagent (Lysis buffer, Ultra-Glo Recombinant Luciferase, Luciferine and Mg2+). Luminescence was measured using a Glomax Multidetection System (Promega).

Wound Healing and Tube Formation Assay

In vitro-scratched wounds were created by scraping confluent HUVEC-1 monolayers in P-24 plate wells with sterile disposable pipet tips. The remaining cells were washed with PBS and incubated with EGM-2 (Lonza) in the absence or presence of propranolol/ICI 118,551 100 μM for up to 6-8 h. For tube formation assays, HUVECs were plated as before but on Matrigel plate ((BD Biosciences, Bedford, Mass., USA) and incubated at 37° C., without and with propranolol/ICI 118,551 treatment (100 μM). Tube formation was monitored for up to 8 hours.

Hemangiospheres Formation and Culture

VHL-derived hemangioblastoma cells were grown in suspension in phenol red free DMEM:F-12 medium with GlutaMAX, supplemented with B27, 20 ng/ml EGF, 20 ng/ml bFGF and 1% penicillin/streptomycin at 37° C. in 5% CO2. Single cell suspensions were plated at a density of 50.000 cells/ml in 75 cm² ultralow attachment flasks (Corning). Cultures were untreated or treated with propranolol/ICI 118,551 at the shown concentrations.

Cell Viability Measure

Endothelial cell lines (HUVECs and HMECs), human ccRCC Vhl-/- 786-O cell line, and primary cultures hemangioblastomas from patients (Hb14 and 18) were seeded in triplicate onto a 96-well plate (2×10³ per well). The next day, cells were treated with vehicle or various mM concentrations of propranolol or ICI-118,551 for 72 hours. Cell viability (cell proliferation, ATP content) was determined using the CellTiter-Glo Luminescent Cell Viability Assay kit (Promega) according to the supplier's instructions. Cell Titer-Glo reagent (Lysis buffer, Ultra-Glo Recombinant Luciferase, Luciferine and $Mg^{2+}$). Cell lysis was induced in an orbital shaker for 2 min, and then plates were incubated at room temperature for 10 min to stabilize the luminescent signal. Luminescence was measured using a GlomaxMultidetection System (Promega) Readings were normalized to control (100%).

Xenografts of 786-O Human ccRCC Cells in Mice

Male 7-8 weeks old NOD scid gamma (NSG) mice were injected in the dorsal flank with a single cell suspension of 106 786-O cells. When tumor size reached 100 mm$^3$ volume, mice were randomly divided in 3 groups, of 9/10 mice each. Two groups were daily treated intraperitoneally with 10 mg/Kg body propranolol or ICI-118,551, respectively and a third group was injected with the solvent. Tumor size was measured by a caliper every 2-3 days and volumes were calculated following the formula: shortest 2×largest×0.52. Mice were sacrificed when tumor volume average of the control group reached an end point established according to ethical procedures Results ICI 118,551 Decreases Viability of Hemangioblastoma and Inhibits Hemangiosphere Formation from VHL Patients Results shown in examples demonstrate that ICI 118,551, a selective beta 2 blocker, not only mirrors the results obtained with propranolol (non-selective beta blocker which binds beta 1 and beta 2 receptors) (see Albiñana et al., Orphanet J of are diseases. 10:118 (2015)) but also shows superior results to propranolol. In particular, for the case of VHL-tumor derived cells, ICI 118,551 decreases viability by an increase in cell apoptosis, inhibits hemangiosphere formation, which is a specific property of tumors containing undifferentiated stem cells, and is an antiangiogenic agent through the inhibition of HIF-stimulated transcription of its target genes.

Propranolol and ICI 118,551 decrease viability of hemangioblastoma cells from a primary culture derived from a VHL tumor by at least 55-60% compared to the same untreated cells (FIG. 1). In most cases the effect of ICI 118,551 is superior to propranolol, when both are used at 100 μM, after 72 hours of treatment. The decrease of viability ranges from 60 to 40% depending of different tumors, patients and time of culture.

FIG. 2 presents the remaining cells in cultures after 72 hours of treatment with P (propranolol 100 μM) and ICI 118,551 50 μM (HB 18) and 100 μM in (HB 4), compared with Control (untreated cells of different hemangioblastomas from 2 different patients). There is a significant reduction in the number of cells of up to 30-40% with respect to the untreated ones. The decrease is due to apoptosis as shown for ICI 118,551 in FIG. 3. FIG. 3 shows the amount of mRNA from two proapoptotic genes, Bax and the executor protease Caspase 9, which is significantly upregulated after cell treatment with ICI 118,551 at 100 μM.

One characteristic of tumoral cells in culture is the property of forming organized spheres around a nucleus of undifferentiated stem cells, these spheres have a well defined border surrounded by an ordered interface with the medium. Antitumoral agents inhibit or disrupt the formation of the spheres by disaggregation of the cells. FIG. 4 is showing hemangiosphere cultures from different hemangioblastomas without treatment and upon 100 μM of either Propranolol or ICI 118,551 treatment for 7 days in these particular cases shown in this FIGS. 4 and 5. As shown in 5 different tumor cultures, hemangiospheres are disrupted by beta-blockers treatment, being especially conspicuous the case of hemangioblastoma 4 (FIG. 4B) and 23 (FIG. 4C) after 100 μM ICI 118,551.

Angiogenesis is the property endothelial cells have to form vessels from preexisting ones. For angiogenesis it is necessary migration of endothelial cells (involving disruption on cell matrix), and tubulogenesis or formation of new tubes (vessels). These properties may be studied in vitro by the test of wound healing (FIG. 5), and matrigel tubulogenesis (FIG. 6).

If confluent monolayers of endothelial cells are disrupted by scratching their surface, the endothelial cells tend to migrate and fill the discontinuity. This "so-called" wound healing test may be followed over time to monitor the migration of cells. FIG. 5A shows how ICI 118,551 and propranolol at 100 μM delay the closure of the discontinuity as compared to untreated cells (control). The migration of untreated cells is faster as quantified in the graph of FIG. 5B, while both ICI 118,551 and propranolol are significantly interfering with the migration process.

FIG. 6A is showing the characteristic network of tubules imitating the capillary network formed by endothelial cells in matrigel after 3 hours. However, if cells are pretreated with ICI 118,551 or Propranolol (100 μM), the number of closed structures is dramatically decreased. The average quantification of closed cells in five different fields is shown in FIG. 6B. It is clear that propranolol and ICI 118,551 are functioning as inhibitors of angiogenesis.

Angiogenesis is largely dependent of HIF transcription program, triggered in the presence of hypoxic condition, or as in the case of Von Hippel Lindau haemangioblastoma cells, due to the lack of VHL protein in charge of targeting HIF protein for its proteasome processing under normoxic conditions in wild type cells. A special peculiarity of hemangioblastoma cells, and clear cell kidney carcinoma cells, is that they constitutively express HIF protein, which is active, and is translocated to nucleus where it may bind and activates its gene targets such as: VEGF, PDGF, EPO, endoglin, several metalloproteases, carbonic anhydrase, Glut-1 and so on. To test that propranolol and ICI 118,551 are inhibitors of HIF transcriptional activity a system of luciferase reporter under the control of nine copies in tandem of the hypoxia responsive element (HRE) followed by luciferase was used. HeLa 9XHRE cells were stably transfected with a HREluc reporter. To induce hypoxic conditions, HeLa cells were cultured with 100 μM desferrioxamine (DFO) (chemical hypoxia). These hypoxic cells were either untreated or treated with 100 μM of either Propranolol or ICI 118,551, and the luciferase activity measured by luminometry. FIG. 7 shows how luciferase expression is triggered under hypoxic conditions, and how this upregulation is dampened by Propranolol and ICI 118,551. ICI 118,551 is clearly superior to Propranolol in abolishing completely the luciferase activity induced by hypoxia, therefore ICI 118,551 is targeting the transcriptional activity of HIF, which is reduced practically to "0". Propranolol and ICI 118,551 are Interfering with the Hypoxia Pathway, Mainly Through the Blockade of the Beta 2 Adrenergic Receptors When HeLa cells harbouring the HRE-luciferase hypoxia reporter are treated with DFO (deferroxiamine), HIF is translocated to the nuclei, and binds the HRE (Hypoxia Responsive Elements) fused to Luciferase reporter, and the stimulation of hypoxia target maybe quantified by luminescence. However, the hypoxia stimulation is extremely reduced in the presence of ICI118,551 and propranolol at 100 μM. As both are Beta 2 adrenergic receptor blockers, atenolol, a specific beta 1 adrenergic blocker was also used. As shown in FIG. 8, atenolol, hardly reduced the hypoxia stimulation. Accordingly, it seems that ICI118,551 is mimicking propranolol targeting HIF-inducible pathway, and the action is carried out by blocking beta 2 type receptor. VHL derived tumors, have a constitutive HIF expression, therefore, the therapeutic effect of ICI118,551 a specific beta 2 blocker, for the von Hippel Lindau disease is explained by a decrease of stimulation of the HIF gene program. Thus, ICI 118,551 mimicks the effects of propranolol interfering with the hypoxia pathway, mainly through the blockade of the beta 2 adrenergic receptors.

ICI 118,551 is Preferentially Targeting Vhl−/− Tumoral Cells, Versus Non Tumoral Cells as HUVECs and HMECs When Vhl−/− cells, primary cultures of hemangioblastoma cells from VHL patients, including the Vhl−/− renal carcinoma cell line 786-O are treated at different doses from 0 to 250 µM of Ser. No. 10/118,551, they are more sensitive than non tumoral cells like HUVECs (Human umbilical vein endothelial cell) and HMECs (human microvasculature endothelial cells). While LD50 for VHL hemangioblastomas is between 50 and 100 µM ICI118,551, in 786-O is 100 µM., in the case of HUVEC and HMEC is around 150 µM. This is very important in order to selectively target the Vhl−/− cells at an ICI118,551 dose below the toxic range for non Vhl−/− cells. See FIG. 9. Thus, ICI 118,551 is preferentially targeting Vhl−/− tumoral cells, versus non tumoral cells.

ICI 118,551 and Propranolol Act Decreasing the Tumor Growth of a ccRCC Vhl−/− 786-O Xenograft in NSG Mice, an In Vivo Model NSG mice treated with propranolol or ICI118,551 (Beta-blockers) inhibits the tumor growth, as shown from significant differences found between the size of the tumors, between 50-60 days after the cell inoculation (FIG. 10). There were no significant differences between propranolol and ICI118,551 treatments, while these treatments showed a significant decrease around 30% of the size tumor versus vehicle treated mice. There were no toxic or adverse effects observed during the time of the treatment. Thus, ICI118,551 acts decreasing the tumor growth of a ccRCC Vhl−/− 786-O xenografts in an in vivo model of NSG mice.

ICI 118.551 Affects Differentially Vhl−/− Cells and Normal Endothelial Cells HUVECs and HMECs.

Primary culture of Haemangioblastoma from VHL, normal primary endothelial HUVECs, and the non tumoral microendothelial cell line HMEC-1 were cultured in the absence or presence of different concentrations of ICI 118.551 (50-250 µM) to measure viability. According to viability curves Haemangioblastoma (HB) cells show only 20% of viability at 100 µM, while HUVEC or HMEC-1 non tumoral cells show 80% and 55% respectively decrease in viability at 100 µM in both cultures, Propranolol and ICI 118,551 have a double way of action: on one hand, they are promoting apoptosis and in this way stopping growth and causing cell death in a programmed way. On the other hand, they are abrogating the transcriptional activation of HIF inducible program, decreasing in this way the expression of target genes such as VEGF, EPO, endoglin, metalloproteases and so on.

The invention claimed is:

1. A method of treatment of von Hippel-Lindau disease in a patient comprising administering to said patient a therapeutically effective amount of a selective antagonist of the B2-adrenergic receptor selected from a compound of formula (II)

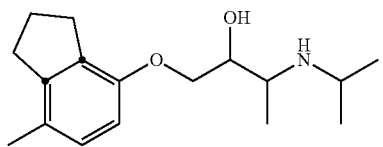

(II)

or a pharmaceutically acceptable acid-addition salt thereof, and
wherein said patient has a heterozygous germline pathogenic von Hippel-Lindau disease variant.

2. The method according to claim 1, wherein the von Hippel-Lindau disease occurs with the appearance of one or more tumors.

3. The method according to claim 2, wherein each of the one or more tumors is a hemangioblastoma.

4. The method according to claim 3, wherein the hemangioblastoma is a retinal hemangioblastoma or a central nervous system hemangioblastoma.

5. The method according to claim 1, wherein the pharmaceutically acceptable acid-addition salt is hydrochloride.

6. The method according to claim 1, wherein the selective antagonist of the $\beta_2$-adrenergic receptor of formula (II) is administered at a dose between 0.2 mg/Kg of body weight/day and 5 mg/kg of body weight/day.

7. The method according to claim 6, wherein the selective antagonist of the $\beta_2$-adrenergic receptor of formula (II) is administered at a dose between 0.5 mg/Kg of body weight/day and 1 mg/kg of body weight/day.

8. The method according to claim 7, wherein the selective antagonist of the $\beta_2$-adrenergic receptor of formula (II) is administered at a dose of 0.8 mg/kg of body weight/day.

9. The method according to claim 1, wherein the selective antagonist of the $\beta_2$-adrenergic receptor of formula (II) is administered intraperitoneally.

10. The method according to claim 1, wherein the selective antagonist of the $\beta_2$-adrenergic receptor of formula (II) is administered daily for 25 days.

11. A method of preserving the health of a patient susceptible to von Hippel-Lindau disease in a patient comprising administering to said patient, before onset of von Hippel-Lindau disease in said patient, a therapeutically effective amount of a selective antagonist of the B2-adrenergic receptor selected from a compound of formula (II)

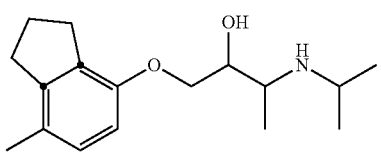

(II)

or a pharmaceutically acceptable acid-addition salt thereof,
wherein said patient has a heterozygous germline pathogenic von Hippel-Lindau disease variant.

12. The method according to claim 11, wherein the pharmaceutically acceptable acid-addition salt is hydrochloride.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: 18S qPRC forward primer

<400> SEQUENCE: 1
ctcaacacgg gaaacctcac                                              20

<210> SEQ ID NO 2
<211> LENGTH: 20
<212> TYPE: DNA
<213> ORGANISM: Artificial Sequence
<220> FEATURE:
<223> OTHER INFORMATION: 18S qPRC reverse primer

<400> SEQUENCE: 2
cgctccacca actaagaacg                                              20

<210> SEQ ID NO 3
<211> LENGTH: 18
<212> TYPE: DNA
<213> ORGANISM: Artificial Sequence
<220> FEATURE:
<223> OTHER INFORMATION: BAX qPCR forward primer

<400> SEQUENCE: 3
cactcccgcc acaaagat                                                18

<210> SEQ ID NO 4
<211> LENGTH: 18
<212> TYPE: DNA
<213> ORGANISM: Artificial Sequence
<220> FEATURE:
<223> OTHER INFORMATION: BAX qPCR reverse primer

```
<400> SEQUENCE: 4
caagaccagg gtggttgg                                                18

<210> SEQ ID NO 5
<211> LENGTH: 20
<212> TYPE: DNA
<213> ORGANISM: Artificial Sequence
<220> FEATURE:
<223> OTHER INFORMATION: CASP9 qPCR forward primer

<400> SEQUENCE: 5
cccaagctct ttttcatcca                                              20

<210> SEQ ID NO 6
<211> LENGTH: 19
<212> TYPE: DNA
<213> ORGANISM: Artificial Sequence
<220> FEATURE:
<223> OTHER INFORMATION: CASP9 qPCR reverse primer

<400> SEQUENCE: 6
ttactgccag gggactcgt                                               19
```